United States Patent [19]
Okano et al.

[11] Patent Number: 5,681,803
[45] Date of Patent: Oct. 28, 1997

[54] DETERGENT COMPOSITION HAVING LOW SKIN IRRITABILITY

[75] Inventors: Tomomichi Okano, Chiba; Masahiro Fukuda, Narashino; Junko Tanabe, Tachikawa; Masato Ono, Tokyo; Yasuhiro Akabane, Kawasaki; Hisao Takahashi, Asaka; Naoyuki Egawa, Tokyo; Takenobu Sakatani, Chiba; Hirofumi Kanao; Yuji Yoneyama, both of Funabashi, all of Japan

[73] Assignee: Lion Corporation, Japan

[21] Appl. No.: 347,440

[22] PCT Filed: Jun. 16, 1993

[86] PCT No.: PCT/JP93/00811

§ 371 Date: Nov. 22, 1994

§ 102(e) Date: Nov. 22, 1994

[87] PCT Pub. No.: WO93/25646

PCT Pub. Date: Dec. 23, 1993

[30] Foreign Application Priority Data

Jun. 17, 1992 [JP] Japan ................... 4-183144
Dec. 10, 1992 [JP] Japan ................... 4-352707
Dec. 10, 1992 [JP] Japan ................... 4-352980
Dec. 10, 1992 [JP] Japan ................... 4-352981
Dec. 10, 1992 [JP] Japan ................... 4-352982
Dec. 10, 1992 [JP] Japan ................... 4-352983

[51] Int. Cl.$^6$ ............................................. C11D 17/00
[52] U.S. Cl. .................. 510/130; 510/137; 510/155; 510/156; 510/405; 510/426; 510/429; 560/247; 554/97
[58] Field of Search ........................... 252/550, 553, 252/549, 551; 560/247, 552

[56] References Cited

U.S. PATENT DOCUMENTS 2,078,516  7/1937  Tulleners ..................... 260/99.12
2,127,641  7/1938  Cremer et al. ................ 260/400

(List continued on next page.)

FOREIGN PATENT DOCUMENTS 0054724  6/1982  European Pat. Off. ..
0295535  12/1990 European Pat. Off. ..

(List continued on next page.)

Primary Examiner—Paul Lieberman
Assistant Examiner—Necholus Ogden
Attorney, Agent, or Firm—Lorusso & Loud

[57] ABSTRACT

There is disclosed a detergent composition containing, as an essential ingredient, at least one member selected from three types of α-sulfo-fatty acid derivatives as represented by following formulas (1), (2) and (3):

$$R_1CHCOO(AO)_pH \atop | \atop SO_3M_1 \qquad (1)$$

$$R_2CHCOO(AO)_mCOCHR_3 \atop | \qquad\qquad\qquad | \atop SO_3M_2 \qquad\qquad SO_3M_3 \qquad (2)$$

$$R_4CHCOO(AO)_nR_5 \atop | \atop SO_3M_4 \qquad (3)$$

where $R_1$, $R_2$, $R_3$ and $R_4$ are each an alkyl group or an alkenyl group, each having from 6 to 24 carbon atoms;

$R_5$ is an alkyl group having from 1 to 4 carbon atoms;

$M_1$, $M_2$, $M_3$ and $M_4$ are each a hydrogen atom or a cation capable of forming a salt;

AO is an oxyalkylene group or a polyvalent alcohol residue; and p, m and n are each a positive number.

The detergent compositions are very low in irritability to the body and have a low critical micelle concentration and a low Krafft point. Further, they are highly soluble in water and they can be used in the form of powder or liquid.

20 Claims, 2 Drawing Sheets

U.S. PATENT DOCUMENTS

| | | | |
|---|---|---|---|
| 3,808,200 | 4/1974 | Bistline et al. | 260/234 R |
| 4,472,282 | 9/1984 | Ramachandran et al. | 252/8.7 |
| 4,543,204 | 9/1985 | Gervasio | 252/531 |
| 4,705,644 | 11/1987 | Barone et al. | 252/551 |
| 4,707,289 | 11/1987 | Ramachandran et al. | 252/135 |

FOREIGN PATENT DOCUMENTS

| | | |
|---|---|---|
| 3941061 | 6/1991 | Germany . |
| 3941365 | 6/1991 | Germany . |
| 9029084 | 10/1989 | Japan . |
| 490486 | 5/1970 | Switzerland . |
| 705408 | 5/1951 | United Kingdom . |
| 9008181 | 7/1990 | WIPO . |
| 9206952 | 4/1992 | WIPO . |
| 9207054 | 4/1992 | WIPO . |

DETERGENT COMPOSITION HAVING LOW SKIN IRRITABILITY

TECHNICAL FIELD

The present invention relates to a detergent composition having a remarkably low degree of irritability to the skin of the body, a high degree of resistance to hard water, a low critical micelle concentration (cmc), and a low Krafft point.

BACKGROUND ART

A large number of anionic surface-active agents have been used as detergents on the basis of their excellent surface-active characteristics. The anionic surface-active agents that can be used as detergents for washing kitchen appliances such as dishes shampoos for washing or rinsing the body or the hair are required to be extremely low in the irritability to the skin of the human body because they are always used in a state that they are in contact with the skin of the human body. Hence, a number of those anionic surface-active agents as being used in contact with the body should be limited and they may include, for example, polyoxyethylene alkyl-sulfuric acid esters, alpha-olefin sulfonic acid esters, acidic N-acyl amino acids, alkyloyl alkyl taurine salts, acyl isethionates, alkyl ether carboxylic acids, higher fatty acids, alkyl phosphoric acid ester and alkyl sulfuric acid esters.

On the other hand, recently, alpha-sulfo-fatty acid methyl esters catch an increasing attention in terms of their cleansing performance in the field of detergents for washing clothes, which are not required to be used in contact with the skin of the human body. The alpha-sulfo-fatty acid methyl esters have received a growing attention in the field of the detergents for washing the clothes because they are to be prepared from natural fats oil, such as palm oil.

However, if the alpha-sulfo-fatty acid methyl esters are used for detergents for washing dishes and other kitchen appliances such as dishes and for washing the body or the hair, which are required to be employed in contact with the human body, those detergents suffer from the disadvantage because the alpha-sulfo-fatty acid methyl esters are irritable to the human body. For such reasons, the alpha-sulfo-fatty acid methyl esters are not applied to a sufficient extent to the detergents for washing kitchen appliances. If it would be possible to single out a surface-active alpha-sulfo-fatty acid methyl ester having a low degree of irritability to the skin or the body, useful for the kitchen appliances and applicable to a variety of fields, from the alpha-sulfo-fatty acid methyl esters for the detergents, the alpha-sulfo-fatty acid methyl esters are extremely advantageous from the industrial point of view because they are prepared from raw materials rich in the tropical area of the world.

U.S. Pat. No. 3,808,200 discloses esters of alpha-sulfo fatty acids with mannitol, sorbitol, glucose or sucrose.

CH-A-490486 discloses esters of alpha-sulfo fatty acids with a glycol, glycerine or a polyalkylene glycol.

DE-A-3941061 discloses esters of alpha-sulfo fatty acids with sorbitol.

GB-A-705408 and DE-A-3941365 disclose esters of alpha-sulfo fatty acids with glycerine.

WO-A-9008181 and EP-A-295535 disclose alpha-sulfonic acid derivatives of the formula $C_mH_{2m-1}$—CO—$(OM)_x$—OR (R=alkyl, OM=oxyalkylene).

DISCLOSURE OF INVENTION

The primary object of the present invention is to provide a detergent composition having a low degree of irritability to the skin and containing an anionic surface-active agent which is selected from the alpha-sulfo-fatty acid derivatives having a low degree of irritability to the skin of the human body and having a high degree of surface-active performance.

Another object of the present invention is to provide a detergent composition having a low degree of irritability to the skin and showing a high degree of resistance to hard water during washing.

A further object of the present invention is to provide a detergent composition having a low degree of irritability to the skin, exhibiting a high degree of washing performance, and having a low critical micelle concentration.

A still further object of the present invention is to provide a liquid detergent composition having a low degree of irritability to the skin, having a low Krafft point, and showing stability at low temperature.

Another further object of the present invention is to provide a powdery or granular detergent composition having a low degree of irritability to the skin, showing a high degree of washing or cleansing performance, and having a high extent of solubility in water.

Another still further object of the present invention is to provide an industrially advantageous process for the preparation of a mixture of particular alpha-sulfo-fatty acid derivatives useful as an surface-active ingredient of the detergent composition having a low degree of irritability to the skin.

The other objects, features and advantages of the present invention will become apparent in the course of the description that follows, with reference to the accompanying drawings.

BRIEF DESCRIPTION OF DRAWINGS

In FIG. 2, a sign "•-•" indicates the instance in which diethylene glycol is contained and a sign "o-o" indicates the instance in which diethylene glycol is not contained.

BEST MODE FOR CARRYING OUT THE INVENTION

Figure 2:
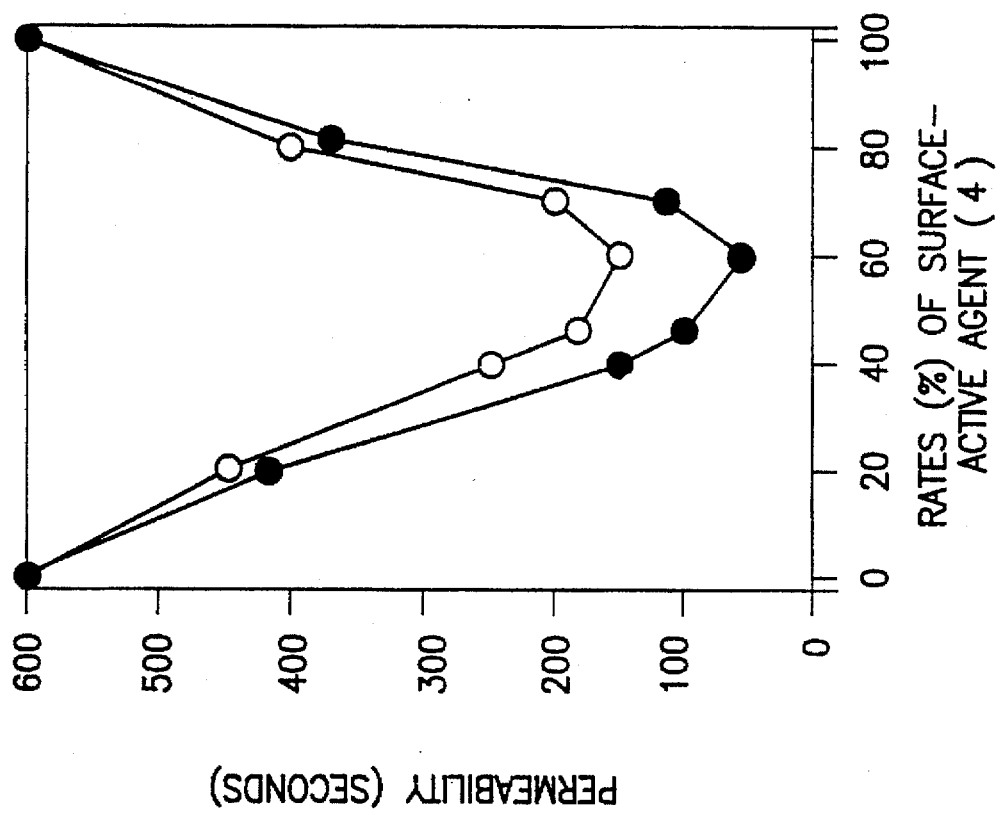
FIG. 2 is a graph showing the relationship of the rates (%) of the surface-active agent (4) contained in the detergent composition vs. permeability (in seconds).

As a result of extensive research and studies with the attempt to develop a detergent composition having a low degree of irritability to the skin of the body, it has been found that an alpha-sulfo-fatty acid derivative having a particular structure can show a very low degree of irritability to the skin and it is greatly advantageous for the preparation of detergent compositions having a low degree of irritability to the skin, a low critical micelle concentration and a low Krafft point, and demonstrating high washing and cleansing performance and high stability in a low temperature range.

The present invention provides a detergent composition comprising an essential ingredient which is at least one member selected from alpha-sulfo-fatty acid derivatives represented by the following formulas (2) and (3):

(2)

(3)

wherein $R_2$ and $R_3$ are each an alkyl group or an alkenyl group, each having from 6 to 24 carbon atoms;

$R_4$ is an alkyl group having from 6 to 24 carbon atoms;

$R_5$ is an alkyl group having from 1 to 4 carbon atoms;

$M_2$, $M_3$ and $M_4$ are each a hydrogen atom or a cation capable of forming a salt;

AO is an oxyalkylene group; and m and n are each a positive integer.

In another aspect, the present invention provides a process for the preparation of a mixture of alpha-sulfo-fatty acid derivatives represented by the formula (2) and the following formula (1):

(1)

wherein $R_1$ is an alkyl group or an alkenyl group having from 6 to 24 carbon atoms;

$M_1$ is a hydrogen atom or a cation capable of forming a salt;

AO is an oxyalkylene group; and p is a positive integer, comprising reacting an alpha-sulfo-fatty acid alkyl ester represented by the following general formula (4):

(4)

wherein $R_6$ is an alkyl group or an alkenyl group, each having from 6 to 24 carbon atoms; and $R_7$ is an alkyl group having from 1 to 3 carbon atoms, with a glycol selected from alkylene glycols and polyalkylene glycols at a temperature of from 80° C. to 150° C.

The symbols $R_1$, $R_2$, $R^3$ and $R^6$ in the general formulas (1), (2), (3) and (4) are each an alkyl group or an alkenyl group having from 6 to 24 carbon atoms, preferably an alkyl group or an alkenyl group having from 8 to 18 carbon atoms. $R_4$ is an alkyl group having 6 to 24 carbon atoms. The alkyl group and the alkenyl group may be each straight or branched. Specific examples of the symbols $R_1$, $R_2$, $R^3$, $R_4$ and $R^6$ may include, for example, octyl, decyl, dodecyl, tetradecyl, hexadecyl and hexadecenyl.

The symbols $M_1$, $M_2$, $M_3$ and $M_4$ in the general formulas (1), (2), and (3) are each a hydrogen atom or a cation capable of forming a salt. The cation capable of forming the salt may include, for example, an ion of an alkali metal such as sodium, potassium, lithium or the like; an ion of an alkaline earth metal such as magnesium, calcium or the like; an ammonium ion derived from ammonia; and a substituted ammonium ion derived from a variety of an organic amine such as trimethylamine, triethylamine, monoethanolamine, diethanolamine, triethanolamine, lysine or the like.

The symbol AO in the general formulas (1), (2) and (3) is an oxy-alkylene group. The oxy-alkylene group may preferably be an oxy-alkylene group having from 2 to 4 carbon atoms. Specific examples of the oxy-alkylene group may include, for example, oxy-ethylene and oxy-propylene. An ether group as represented by symbol $(AO)_p$, $(AO)_m$, or $(AO)_n$ include, for example, a single ether group as represented by symbol $(C_2H_4O)_q$— (where symbol q is a positive number), $(C_3H_6O)_r$— (where symbol r is a positive number), or a mixed ether group as represented by symbol $(C_2H_4O)_q.(C_3H_6O)_r$— (where the symbols q and r are each a positive number). The symbols p, m and n as represented by the general formulas (1), (2) and (3) hereinabove are each the positive number ranging preferably from 1 to 50, more preferably from 1 to 15.

Among the alpha-sulfo-fatty acid derivatives as represented by the general formulas (1), (2) and (3) hereinabove, the alpha-sulfo-fatty acid derivatives as represented by the general formula (2) are the most suitable ones for achieving the objects of the present invention. The alpha-sulfo-fatty acid derivatives as represented by the general formula (2) hereinabove are extremely low in irritability to the skin and have the remarkable characteristic that a critical micelle concentration is low. On the other hand, the alpha-sulfo-fatty acid derivatives as represented by the general formulas (1), (2) and (3) hereinabove present the remarkable feature that a Krafft point is extremely low and resistance to hard water is extremely high.

A mixture of the alpha-sulfo-fatty acid derivatives as represented by the general formulas (1) and (2) hereinabove can conveniently be prepared by subjecting a solution of the alpha-sulfo-fatty acid alkyl ester as represented by the general formula (4) hereinabove in a glycol selected from alkylene glycols and polyalkylene glycols to ester interchange reaction at a temperature range of from 80° C. to 150° C.

A lower alcohol-alpha-sulfo-fatty acid ester as represented by the general formula (4) is not restricted to a particular one as long as it is synthesized by conventional methods. It may preferably be bleached with a bleaching agent such as hydrogen peroxide or the like after synthesis. The method of bleaching is not restricted and any conventional bleaching procedures can preferably be applied.

The glycols to be used as one of the raw materials for the preparation of the alpha-sulfo-fatty acid derivatives as represented by the general formulas (1), (2), and (3) are preferably as follows:

(5)

(where symbol m is a number ranging from 1 to 50);

(6)

(where symbol m is a number ranging from 1 to 15);

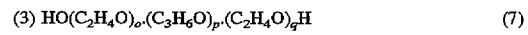
(7)

(where symbols o, p and q are each 0 or 1 or a number larger than 1, provided that the sum of o+p+q is a number ranging from 2 to 15).

As the glycols, there may preferably be used, for example, a poly-oxyalkylene glycol, 1,2-propane diol, 1,3-propane diol, 1,4-butane diol, 1,2-butane diol, 1,5-pentane, 1,6-hexane diol, 1,2-hexane diol, poly-butylene glycol or di-butylene glycol.

Specific examples of glycols preferably employed for the ester interchange reaction may include, for example, polyethylene glycol, di-ethylene glycol, tetra-ethylene glycol, polyethylene glycol #200, #300, #400, #1500, propylene glycol, dipropylene glycol, tri-propylene glycol, ADEKA® polyether series P-400, P-700 (Asahi Denka Kogyo K.K.), PLURONIC® L-31, L-61, L-62, L-84, L-86 (Asahi Denka Kogyo K.K.).

The oxyalkylene-alpha-sulfo-fatty acid esters to be employed for the present invention can be prepared by subjecting the lower alcohol-alpha-sulfo-fatty acid ester and the glycol to ester interchange reaction.

The ester interchange reaction of the alpha-sulfo-fatty acid alkyl ester as represented by the general formula (4) with the glycol may be carried out as the first step by mixing the lower alcohol-alpha-sulfo-fatty acid ester with the glycol and dissolving the former in the latter at temperature ranging from 30° C. to 80° C., preferably from 40° C. to 60° C. In the first step, there may be employed, as needed, an organic solvent having a boiling point of 200° C. or lower, such as a lower alcohol, e.g. methanol, ethanol or propanol. As a promoter for dissolving the lower alcohol-alpha-sulfo-fatty acid ester in the glycol. The second step of the ester inter change reaction involves heating the resulting solution to a temperature range of from 80° C. to 150° C., preferably from 85° C. to 115° C., more preferably from 95° C. to 110° C., at which the ester interchange reaction is allowed to proceed. In this instance, if the reaction temperature does not reach 80° C., the viscosity of the reaction mixture may becomes too high to proceed with the reaction in a smooth way. If the temperature would exceed 150° C., the color of the reaction mixture may turn darker. Although the ester interchange reaction can be carried out at ambient pressure, it is preferred to carry out the reaction under reduced pressure, preferably at pressure reduced to 200 torr (266.64 hPa) or lower, in order to distill off a lower alcohol produced during the reaction from the reaction system.

The molar ratio of the lower alcohol-alpha-sulfo-fatty acid ester to glycol at the time of charging the raw materials may range usually from approximately 1:3 to 3:1, preferably from approximately 1:2 to 2:1. If the molar ratio would be outside the range as defined hereinabove, a large volume of the lower alcohol-alpha-sulfo-fatty acid ester or the glycol may be left so unreacted that this may cause the problem for the ester interchange reaction.

When the poly-alkylene glycol is used as the glycol for the ester interchange reaction, there may be formed a poly-alkylene glycol-alpha-sulfo-fatty acid mono-ester and a poly-alkylene glycol-alpha-sulfo-fatty acid di-ester. The molar ratio of the poly alkylene glycol-alpha-sulfo-fatty acid mono-ester to the poly-alkylene glycol-alpha-sulfo-fatty acid di-ester can readily be adjusted by changing the molar ratio of the lower alcohol-alpha-sulfo-fatty acid ester to the glycol at the time of charging the raw materials. More specifically, when the lower alcohol-alpha-sulfo-fatty acid ester is charged so as to increase the molar ratio of the lower alcohol-alpha-sulfo-fatty acid ester to the glycol, on the one hand, the amount of the resulting poly-alkylene glycol-alpha-sulfo-fatty acid di-ester can be increased. When the poly-alkylene glycol to be used as the glycol is increased, on the other hand, the amount of the resulting poly-alkylene glycol-alpha-sulfo-fatty acid mono-ester is increased.

The lower alcohol-alpha-sulfo-fatty acid esters serve as an acid catalyst as well as the raw material for the reaction so that it is not particularly required to have any catalyst added to the reaction system. Further, a reaction reagent, such as carbon tetrachloride or toluene, which has been otherwise used for conventional methods, is not or little required. Hence, the alpha-sulfo-fatty acid derivatives to be used for the present invention can be advantageously prepared in an economical way and without worsening the environment in which the operations for carrying out the reaction are to be conducted.

In addition, the ester interchange reaction proceeds so fast that the reaction time can be shortened to a great extent. Furthermore, no or little impurities are formed during the ester interchange reaction, thereby causing the reaction products to become little colored and, as a result, producing the reaction products having a good tone of color at a high yield.

In particular, when there is used, as the raw material, the lower alcohol-alpha-sulfo-fatty acid ester which has previously been bleached with a bleaching agent such as hydrogen peroxide or the like, the resulting reaction product is colored to a lesser extent, yielding the reaction product demonstrating a very good tone of color.

The oxyalkylene glycol-alpha-sulfo-fatty acid esters obtained by the ester interchange reaction can be used intact in an acidic state after the reaction has been finished or they can be neutralized into a salt state, as needed, for use as a surface-active agent. They can be neutralized in any conventional procedures. The salt into which the oxyalkylene glycol-alpha-sulfo-fatty acid esters can be neutralized may include, for example, an alkali metal salt such as sodium salt, potassium salt, or the like; an alkaline earth metal salt such as magnesium salt, calcium salt, or the like; ammonium salt, a substituted ammonium salt such as an ammonium salt derived from an organic amine, e.g. a lower amine, a lower alkanol amine, or the like; and so on. Further, they may be post-treated in accordance with their use by adjusting the pH, bleaching or the like.

The ester interchange reaction of the alpha-sulfo-fatty acid alkyl esters, as represented by the general formula (4) hereinabove, with the glycols can provide the oxyalkylene glycol-alpha-sulfo-fatty acid esters, as represented by the general formula (1) or (2) hereinabove, at a high yield in an economically advantageous way, and the resulting reaction products are provided with a good tone of color. The alpha-sulfo-fatty acid esters as represented by the general formula (1) and (2) hereinabove can be prepared, for example, by direct esterification method, acid chloride method or alcolysis, in addition to the ester interchange reaction; however, as these processes may provide the resulting reaction products with a poor tone of color at a poor yield, the ester interchange reaction is preferred. Further, these processes may suffer from the disadvantage that some difficulty is caused to occur in carrying out the reaction.

The oxyalkylene glycol-alpha-sulfo-fatty acid esters, as represented by the general formula (3) hereinabove, can be prepared by subjecting the alpha-sulfo-fatty acid alkyl esters, as represented by the general formula (4) hereinabove, to ester interchange reaction with a partially etherified glycol having one hydroxyl group. Such partially etherified glycols having one hydroxyl group may include, for example, an alkylene glycol mono-alkyl ether, a poly-alkylene glycol mono-alkyl ether, a di-alkyl ether of glycerin, and so on. As these partially etherified glycols contain each one hydroxyl group, the ester interchange reaction can provide the oxyalkylene glycol-alpha-sulfo-fatty acid esters as represented by the general formula (3).

The detergent compositions according to the present invention contain at least one of the alpha-sulfo-fatty acid derivatives as represented by the general formulas, (2) and (3) as an essential ingredient of the surface-active agent. Although the concentration of the alpha-sulfo-fatty acid derivatives in the detergent composition is not restricted to a particular range as long as the resulting detergent composition can demonstrate the effects as the detergent, the concentration of the alpha-sulfo-fatty acid derivatives may range preferably from 1% to 50% by weight, more preferably from, 5% to 40% by weight. Further, an additionally appropriate ingredient or ingredients may be added to the detergent compositions according to the present invention, as needed, as long as it does not or they do not adversely affect the objects of the present invention. To the detergent compositions may be added such ingredients, as needed, which may include, for example, a humectant such as propylene glycol, glycerin or sorbitol; a viscosity modifier such as methyl cellulose, polyoxy-ethylene glycol distearate or ethanol; a preservative or an antiseptic such as methyl-paraben or butyl-paraben; an anti-inflammatory agent such as potassium glycyr-rhizate or tocopherol acetate; a microbicide, a pearling agent, an anti-oxidant, a flavor, a pigment or a ultraviolet absorber.

Furthermore, the detergent compositions according to the present invention may be used together with other surface-active agents which may include, for example, an anionic surface-active agent such as a polyoxy ethylene alkyl ether sulfate, a surface-active agent of an alkyl phosphate ester type, a surface-active agent of an amino acid type, a surface-active agent of a sulfo-succinic acid type, a surface-active agent of a taurine type or a higher fatty acid salt; and a non-ionic surface-active agent such as a surface active agent of an alkyl saccharide type or a polyoxy-ethylene alkyl ether type.

The detergent compositions according to the present invention may preferably contain the alpha-sulfo-fatty acid alkyl mono-ester (A) of the general formula (1) and the alpha-sulfo-fatty acid alkyl di-ester (B) of the general formula (2). The detergent compositions containing the alpha-sulfo-fatty acid methyl ester derivative (A) and the alpha-sulfo-fatty acid di-ester derivative (B) is remarkably superior in permeability to the detergent compositions containing each of them as a sole ingredient. The ratio in weight of the alpha-sulfo-fatty acid methyl mono-ester derivative (A) as represented by the general formula (1) to the alpha-sulfo-fatty acid di-ester derivative (B) as represented by the general formula (2) may preferably range from approximately 5:95 to 95:5, more preferably from approximately 20:80 to 80:20.

Preferably, the detergent compositions according to the present invention may further contain a poly-valent alcohol (C), in addition to the alpha-sulfo-fatty acid methyl mono-ester derivative (A) and the alpha-sulfo-fatty acid di-ester derivative (B). As the poly-valent alcohol (C) there may be mentioned, for example, an alkylene glycol such as ethylene glycol or propylene glycol; a poly-alkylene glycol such as polyethylene glycol or polypropylene glycol; a PLURONIC® compound such as a copolymer of an ethylene oxide with a propylene oxide; a glycerin type compound such as glycerin or poly-glycerin; a sugar alcohol such as glucose or sucrose; pentaerythritol. The poly-valent alcohols (C) may be used in an amount up to approximately 80% by weight, with respect to the total weight of the ingredients (A), (B) and (C). The preferred compositions according to the present inventions may contain the ingredient (A) in an amount of from approximately 10% to 50% by weight, the ingredient (B) in an amount of from approximately 10% to 70% by weight, and the ingredient (C) in an amount of from approximately 5% to 40% by weight, with respect to the total weight of the ingredients (A), (B) and (C).

The detergent compositions according to the present invention may be in the form of liquid in which the alpha-sulfo-fatty acid ester derivatives may be contained in the total concentration ranging from approximately 1% to 50% by weight, preferably from approximately 5% to 40% by weight.

The liquid detergent compositions according to the present invention are anionic liquid detergent compositions that are low in irritability to the human body and excellent in resistance to hard water. They can appropriately be used as detergents that are used in contact with the human body, such as shampoos for washing or cleansing the body or hair and for washing kitchen appliances such as dishes. Further, they are remarkably resistant to hard water so that they can also be used as a heavy liquid detergent and a light liquid detergent.

In addition, the detergent compositions according to the present invention can be used in the form of powder or granules. The powdery or granular detergent compositions may contain the alpha-sulfo-fatty acid ester derivatives in the total concentration ranging from approximately 1% to 50% by weight, preferably from approximately 5% to 30% by weight. In order to improve washing or cleansing characteristics such as washing or cleansing performance, bubbling ability and rinsing ability, the powdery or granular detergent compositions according to the present invention may contain an additional surface-active agent or agents or conventional accessory ingredient or ingredients, such as a builder.

As the other surface-active agents to be used together with the alpha-sulfo-fatty acid derivatives contained in the detergent compositions according to the present invention, there may be mentioned an anionic surface-active agent, a non-ionic surface-active agent, an amphoteric surface-active agent or a cationic surface-active agent. as will be described hereinafter.

As the anionic surface-active agents, there may be mentioned, for example:

1. a straight-chained alkyl benzene sulfonate having an alkyl group having an average carbon atom number of from 8 to 16;

2. an alpha-olefin sulfonate having an average carbon atom number of from 10 to 20;

3. a sulfonate of a fatty acid lower alkyl ester or a di-salt of a sulfonated fatty acid, as represented by the general formula (8):

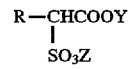

$$R-\underset{SO_3Z}{CHCOOY} \qquad (8)$$

(wherein

R is an alkyl group or an alkenyl group, each having from 8 to 20 carbon atoms;

Y is an alkyl group having from 1 to 3 carbon atoms or a cation capable of forming a salt; and Z is a cation capable of forming a salt, in which the cation may include, for example, an alkali metal ion, such as sodium ion or potassium ion);

4. an alkyl sulfate having an average carbon atom number of from 10 to 20;

5. a sulfuric acid alkyl ether having an alkyl group with an average carbon atom number of from 10 to 20 or a sulfuric acid alkenyl ether having an alkenyl group with an average carbon atom number of from 10 to 20, each having an ethylene oxide added thereto at the average rate of from 0.5 to 8 moles; and 6. a saturated fatty acid or an unsaturated fatty acid, each having an average carbon atom number of from 10 to 20.

As the nonionic surface-active agents, there may be mentioned, for example:

1. an EO adduct type nonionic surface-active agent (an alkyl ether ethoxylate) with ethylene oxide (EO) added to a primary or secondary alcohol having an average carbon atom number of from 8 to 18 at the average rate of from 4 moles to 25 moles;

2. an EO-PO adduct type nonionic surface-active agent with ethylene oxide (EO) added to a primary or secondary alcohol, each having an average carbon atom number of from 8 to 18, at the average rate of from 4 moles to 25 moles and with propylene oxide (PO) thereto at the average rate of from 3 moles to 10 moles; and 3. an ester type nonionic surface-active agent as represented by the general formula (9) below, having ethylene oxide (EO) added to a lower alkyl ester of a fatty acid having an average carbon atom number of from 8 to 18 at the average rate of from 4 moles to 30 moles:

$$RCO(OCH_2CH_2)_nOR'$$

(where

R is an alkyl group or an alkenyl group, each having from 7 to 17 carbon atoms;

R' is an alkyl group having from 1 to 5 carbon atoms; and n is an integer of from 4 to 30).

The ester type nonionic surface-active agent as described hereinabove is an alkyl ether of an alkylene oxide addition product of the fatty acid. The ester type nonionic surface-active agent can be prepared by two steps, the first step involving the addition of an alkylene oxide to the fatty acid and the second step involving the alkyl-etherification of the resulting addition product. Further, the ester type nonionic surface-active agent can also be prepared by one step by reacting a fatty acid alkyl ester, as represented by general formula: RCOOR', with the alkylene oxide in the presence of a catalyst consisting of a magnesium oxide to which there is added at least one metal ion selected from metal ions such as a trivalent aluminum (Al) ion, a gallium (Ga) ion, an indium (In) ion, a thallium (Tl) ion, a cobalt (Co) ion, a scandium (Sc) ion, a lanthanum (La) ion and a divalent manganese (Mn) ion.

The powdery or granular detergent compositions according to the present invention may contain a water-insoluble builder and/or a water-soluble builder. As the water-insoluble builder, there may be mentioned, for example, a zeolite as represented by the general formula (10) as follows:

$$(M_2O)_x \cdot (Al_2O_3) \cdot (SiO_2)_y \cdot (H_2O)_z \qquad (10)$$

(where

M is Na or K;

x is 0.7–1.5;

y is 0.8–6; and z is 0 or an integer of 1 or larger).

The zeolite may preferably have a particle size of 5 μm or smaller. The zeolite to be added to the powdery or granular detergent compositions according to the present invention can function as trapping an ingredient imparting hardness to water, such as calcium ion or magnesium ion, with the aid of its ion exchange capability, thereby improving washing and cleansing performance, exhibiting powdery or granular properties, and preventing the detergent compositions from caking during storage.

As the water-soluble builders, there may be mentioned, for example, a phosphate such as sodium tripolyphosphate or sodium pyrophosphate; an organic chelating builder such as trisodium nitrilotriacetate (NTA) or trisodium citrate; a polymer builder such as a polyacetal carboxylate, an acrylate polymer, a hydroxylacrylate polymer, an acrylate-methacrylate copolymer or an maleic anhydride-oleate copolymer; and an alkali builder such as sodium carbonate, potassium carbonate, sodium silicate or sodium borate. The builders have the ability of trapping calcium ion and magnesium ion or the alkaline buffer ability. They may preferably be formulated with a powdery or granular heavy detergent.

The powdery or granular detergent compositions according to the present invention may further contain an agent for preventing re-staining, such as polyethylene glycol or carboxymethyl cellulose; a reducing agent such as sodium hydrogen sulfite or sodium sulfite; an enzyme such as an alkali protease, amylase, cellulase or lipase; a fluorescent brightening agent; Glauber's salt (salt cake); and a flavor.

The powdery or granular detergent compositions according to the present invention may be produced by forming the mixture of all the detergent composition ingredients into the slurry form and subjecting the resulting slurry to spray-drying, thereby formulating the detergent compositions in the form of hollow beads having a bulk density ranging from 0.2 gram/cc to 0.5 gram/cc. The mixture containing the detergent composition ingredients may be granulated into a composition having a high bulk density ranging from 0.6 gram/cc to 1.2 grams/cc.

The granulation of the detergent compositions according to the present invention may be carried out in the process as disclosed in Japanese Patent Laid-open (Unexamined) Publication No. 60(1985)-96,698. This process can formulate the powdery or granular detergent compositions by kneading or mixing the raw materials for the detergent compositions with a kneader or a mixer, grinding or crushing them in a mill such as a cutter type mill or the like, granulating the finely ground or crushed raw materials into granules, and mixing them with fine powder insoluble in water. The detergent compositions having a high bulk density may be prepared by spray-drying a portion or a whole of the ingredients for the detergent compositions and then kneading or mixing the dried ingredients with the rest of the non-dried ingredients or by spray-drying the ingredients for the detergent compositions, stirring the spray-dried ingredients with an ingredient or ingredients of another detergent, and granulating the resulting mixture into granules. The ingredients such as the enzyme or the builders may be blended in the powder form with the granulated detergent compositions.

The powdery or granular detergent compositions according to the present invention can exhibit a remarkably high solubility and washing or cleansing performance even in a low temperature range.

EXAMPLES

The present invention will be described in more detail by way of examples. In the examples and the comparative examples which follow, the units, parts and %, are represented on a weight basis.

Example 1

The surface-active agents as shown in Table 1 hereinafter are tested for a protein denaturation ratio, resistance to hard water, a critical micelle concentration, and a Krafft point. The tests were carried out in the manner as will be described hereinafter.

1. Test for Measuring the Protein Denaturation Ratio:

A phosphate buffer solution (pH=7.0) containing 100 ppm of bovine serum albumin was added to an aqueous solution containing 1,000 ppm of the surface-active agent to be tested and the resulting mixture was allowed to stand at room temperature for 24 hours. Then, the resulting mixture was measured for its circular dichroism at 220 nm to give the measured value (A). On the other hand, as a comparative purpose, an aqueous mixture containing bovine serum albumin (without containing any surface-active agent) was likewise allowed to stand and then measured for its circular dichroism at 220 nm to give the measured value (B). The protein denaturation ratio was calculated by the following formula:

*Protein Denaturation Ratio (%)=(B−A)/B×100*

The surface-active agent was determined to be lower in irritability to the skin as the protein denaturation ratio, represented in percentage (%), becomes smaller.

2. Test for Measuring Resistance to Hard Water:

A sheet of paper on which letters were typed was attached to the bottom of a 100-ml beaker which in turn was supplied with 40 ml of a 0.5% aqueous solution of the surface-active agent to be tested. Then, a 1% calcium acetate aqueous solution was dropwise added until the letters typed on the paper attached on the bottom of the beaker could not be seen any more. The amount of the calcium acetate aqueous solution was translated into the concentration (ppm) of the calcium acetate. The surface-active agent was determined to be higher in resistance to hard water as the concentration (ppm) of the calcium acetate was larger.

3. Test for the Measurement of Critical Micelle Concentration:

The critical micelle concentration of the surface-active agent was measured in accordance with the measurement process using pinacyanol chloride (refer to Corrin, M. L., Klevens, H. B., Harkins, W. D.: J. Chem. Phy., vol. 14, p. 216 (1946)). The measurement process involves preparing a variety of concentrations of aqueous solutions of the surface-active agent, adding the equal volume of a 2×10−5M pinacyanol chloride aqueous solution to each of the aqueous solutions, and measuring a ultraviolet absorption spectrum for each of the resulting solutions. A critical concentration at which a spectrum pattern inherent in the monomer solution having the maximal absorption peak at 480 nm has changed into a spectrum pattern inherent in the micelle having the maximal absorption peak at 615 nm was determined as the critical micelle concentration.

4. Test for the Measurement of the Krafft Point:

An aqueous solution of the surface-active agent having the concentration higher than the critical micelle concentration was prepared and the temperature at which the surface-active agent was dissolved was visibly observed. The temperature was determined as a Krafft point.

TABLE 1

| SURFACE ACTIVE AGENTS | PROTEIN DENATURATION RATIO (%) | RESISTANCE TO HARD WATER (ppm) | KRAFFT POINT (°C.) | CRITICAL MICELLE CONCENTRATION (mM) |
|---|---|---|---|---|
| GENERAL FORMULA (1) | | | | |
| COMPOUND A* | 2 | ≧1,800 | ≦1 | 7.6 |
| COMPOUND B* | 2 | ≧1,800 | ≦1 | 2.1 |
| COMPOUND C* | 4 | ≧1,800 | ≦1 | 2.4 |
| COMPOUND D* | 3 | ≧1,800 | ≦1 | 0.37 |
| COMPOUND E* | 3 | ≧1,800 | ≦1 | 0.10 |
| GENERAL FORMULA (2) | | | | |
| COMPOUND F | 2 | ≧1,800 | ≦1 | 0.27 |
| COMPOUND G | 2 | ≧1,800 | ≦1 | 0.29 |
| COMPOUND H | 1 | ≧1,800 | ≦1 | 0.34 |
| COMPOUND I | 1 | ≧1,800 | ≦1 | 0.085 |
| COMPOUND J | 1 | ≧1,800 | ≦1 | 0.022 |
| GENERAL FORMULA (3) | | | | |
| COMPOUND K | 4 | ≧1,800 | ≦1 | 2.0 |
| COMPOUND L | 5 | ≧1,800 | ≦1 | 0.52 |
| COMPARATIVE COMPOUND A | 20 | 800 | 17 | 0.73 |
| COMPARATIVE COMPOUND B | 27 | 250 | 16 | 8.5 |
| COMPARATIVE COMPOUND C | 21 | 200 | 30 | 6.3 |

*: Comparative Example

The surface-active agents as indicated by "COMPOUNDS A-O" in Table 1 hereinabove are as follows:

COMPOUND A: Sodium salt of polyoxy ethylene glycol (4.5)-alpha-sulfo-lauric acid mono-ester COMPOUND B: Sodium salt of polyoxy ethylene glycol (9)-alpha-sulfo-myristic acid mono-ester COMPOUND C: Sodium salt of polyoxy ethylene glycol (23)-alpha-sulfo-myristic acid mono-ester COMPOUND D: Sodium salt of polyoxy ethylene glycol (9)-alpha-sulfo-palmitic acid mono-ester COMPOUND E: Sodium salt of polyoxy ethylene glycol (9)-alpha-sulfo-stearic acid mono-ester COMPOUND F: Sodium salt of polyoxy ethylene glycol (2)-alpha-sulfo-myristic acid di-ester COMPOUND G: Sodium salt of polyoxy ethylene glycol (3)-alpha-sulfo-myristic acid di-ester COMPOUND H: Sodium salt of polyoxy ethylene glycol (9)-alpha-sulfo-myristic acid di-ester COMPOUND I: Sodium salt of polyoxy ethylene glycol (9)-alpha-sulfo-palmitic acid di-ester COMPOUND J: Sodium salt of polyoxy ethylene glycol (23)-alpha-sulfo-stearic acid di-ester COMPOUND K: Sodium salt of polyoxy ethylene glycol (3) mono-methyl-ether-alpha-sulfo-myristic acid ester COMPOUND L: Sodium salt of polyoxy ethylene glycol (4) mono-methyl-ether-alpha-sulfo-palmitic acid ester COMPARATIVE COMPOUND A: Sodium salt of alpha-sulfo-palmitic acid methyl ester COMPARATIVE COMPOUND B: Sodium laurylsulfate COMPARATIVE COMPOUND C: potassium myristate

Example 2

The surface-active agents as shown in Table 2 hereinafter are tested for the test for measuring the protein denaturation ratio, the resistance to hard water, the critical micelle concentration, and the Krafft point. The tests were carried out in the manner as has been described in Example 1 hereinabove.

TABLE 2

| SURFACE ACTIVE AGENTS | PROTEIN DENATURATION RATIO (%) | RESISTANCE TO HARD WATER (ppm) | KRAFFT POINT (°C.) | CRITICAL MICELLE CONCENTRATION (mM) |
|---|---|---|---|---|
| COMPOUND M | 1 | >1,800 | <0 | 0.99 |
| COMPOUND N | 2 | >1,800 | <0 | 0.25 |
| COMPOUND O | 2 | >1,800 | 0 | 0.072 |
| COMPOUND P | 2 | 950 | 23 | 0.017 |
| COMPARATIVE COMPOUND A | 21 | 800 | 17 | 0.73 |
| COMPARATIVE COMPOUND B | 27 | 250 | 16 | 8.5 |
| COMPARATIVE COMPOUND C | 27 | 200 | 30 | 6.3 |

The surface-active agents as indicated in Table 2 hereinabove are as follows:

COMPOUND M: Sodium salt of mono-ethylene glycol-alpha-sulfo-lauric acid di-ester COMPOUND N: Sodium salt of mono-ethylene glycol-alpha-sulfo-myristic acid di-ester COMPOUND O: Sodium salt of mono-ethylene glycol-alpha-sulfo-palmitic acid di-ester COMPOUND P: Sodium salt of mono-ethylene glycol-alpha-sulfo-palmitic acid di-ester COMPARATIVE COMPOUND A: Sodium salt of alpha-sulfo-palmitic acid methyl ester COMPARATIVE COMPOUND B: Sodium laurylsulfate COMPARATIVE COMPOUND C: Potassium myristate

Example 3

The surface-active agents as shown in Table 3 hereinafter are assessed for their irritability to the skin and dispersibility in such a manner as will be described hereinafter. The evaluation results are shown in Table 3 hereinafter.

1. Test for Measuring irritability to the skin:

As a test solution, an aqueous solution was prepared so as to contain the surface-active agents to be tested in the quantity of 5% by weight. Twenty test solutions were subjected to the closed batch test by applying them to the upper arm for five days and they were rated as follows:

o=no case of incidence such as turning red, a skin rash, etc

Δ=the number of cases of incidence being one out of 20 test cases

X=the number of cases of incidence being two or more out of 20 test cases

2. Test for Measuring Dispersibility:

As a test sample, there was prepared 50 ml of an aqueous solution containing 0.01% by weight of carbon black and 0.1% by weight of the surface-active agent to be tested, and the resulting solution was stirred for 5 hours in a thermostat bath kept at 25° C., followed by allowing the solution to stand for 24 hours. The dispersibility was rated as follows:

o=carbon black being dispersed in a homogeneous state

Δ=carbon black being dispersed yet in a heterogeneous state

X=carbon black being separated in layers

TABLE 3

| SURFACE-ACTIVE AGENTS | IRRITABILITY | DISPERSIBILITY |
|---|---|---|
| COMPOUND Q | O | O |
| COMPOUND R | O | O |
| COMPOUND S | O | O |
| COMPARATIVE COMPOUND D | X | X |
| COMPARATIVE COMPOUND E | Δ | X |

The surface-active agents as indicated in Table 3 hereinabove are as follows:

COMPOUND Q: Sodium salt of propylene glycol-alpha-sulfo-tauric acid di-ester

COMPOUND R: Sodium salt of butylene glycol-alpha-sulfo-myristic acid di-ester

COMPOUND S: Sodium salt of iso-propylene glycol-alpha-sulfo-stearic acid di-ester COMPARATIVE COMPOUND D: Sodium dodecylsulfate COMPARATIVE COMPOUND E: Sodium salt of palm oil fatty acid soap

Example 4

A mixture was prepared containing tri-ethylene glycol/sodium salt of alpha-sulfo-stearic acid mono-ester (surface-active agent 1) and tri-ethylene glycol/sodium salt of alphasulfo-stearic acid di-ester (surface-active agent 2) so as to give compositions containing a variety of concentrations of the surface-active agents in the ratio of the weight of the surface-active agent 1 to the weight of the surface-active agent 2 ranging from 0:100 to 100:0. The resulting surface-active agent compositions were tested for permeability in accordance with the felt disc permeability process. The felt disc permeability process comprises pouring a 1% (by weight) aqueous solution of each of the surface-active agent compositions into a beaker, maintaining the temperature of the solution at 25° C., placing a 1 cm×1 cm felt disc (AW-8020) on the surface of the aqueous solution, and measuring the time required until the felt disc went down under the surface of the aqueous solution. The time represented in seconds is determined as the permeability. The permeability is considered as being higher as the measured time is shorter. When 10 minutes or more are required until the felt disc sank in the solution, the permeability is set uniformly to 600 seconds. The test results are shown in FIG. 1.

Figure 1:
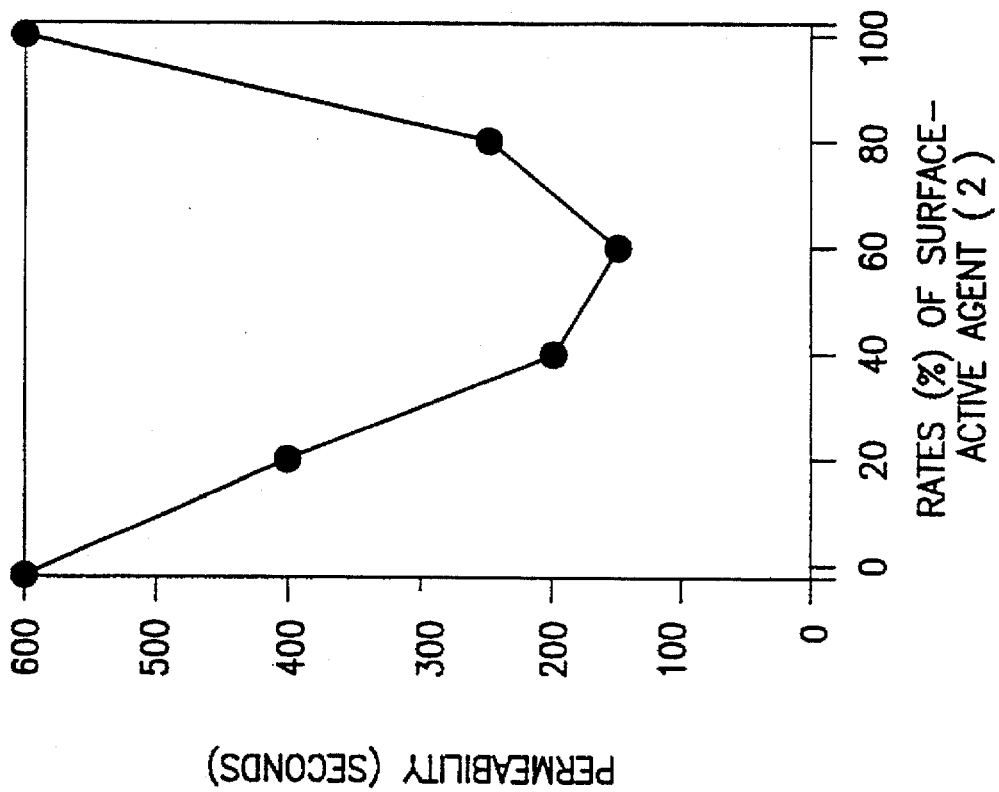
FIG. 1 is a graph showing the relationship of the rates (%) of the surface-active agent (2) contained in the detergent composition vs. permeability (in seconds).

As is apparent from the test results as shown in FIG. 1, it has been found that the mixed compositions containing the surface-active agents (1) and (2) exhibit remarkably improved permeability performance as compared with the composition containing each of the surface-active agent (1) or (2) solely.

Example 5

A mixture was prepared containing a sodium salt of di-ethylene glycol-alpha-sulfo-palmitic acid mono-ester (surface-active agent 3) and a sodium salt of di-ethylene glycol-alpha-sulfo-palmitic acid di-ester(surface-active agent 4) so as to give compositions containing a variety of concentrations of the surface-active agents in the ratio of the weight of the surface-active agent 3 to the weight of the surface-active agent 4 ranging from 0:100 to 100:0. The resulting surface-active agent compositions were tested for permeability in the same manner as in Example 4. The test results are shown in FIG. 2.

As is apparent from the test results as shown in FIG. 2, it has been found that the surface-active agent compositions containing the polyvalent alcohol demonstrate further remarkably improved permeability performance as compared with the composition containing none of the polyvalent alcohol.

Example 6

A mixture was prepared containing a sodium salt of pluronic glycol (EO=6, PO=2)-alpha-sulfo-fatty acid mono-ester (A) and a di-sodium salt of pluronic glycol (EO=6, PO=2)-alpha-sulfo-fatty acid di-ester (B) in the ratio of the ester (A) to the ester (B) of 25 to 75, and there was formulated a composition of the surface-active agent having a variety of chain lengths of the hydrophobic group. The surface-active agent composition was then measured for its permeability in the same manner as in Example 4, thereby determining the influence of the chain length of the alkyl group upon the permeability of the compositions. The test results are shown in FIG. 3.

Figure 3:
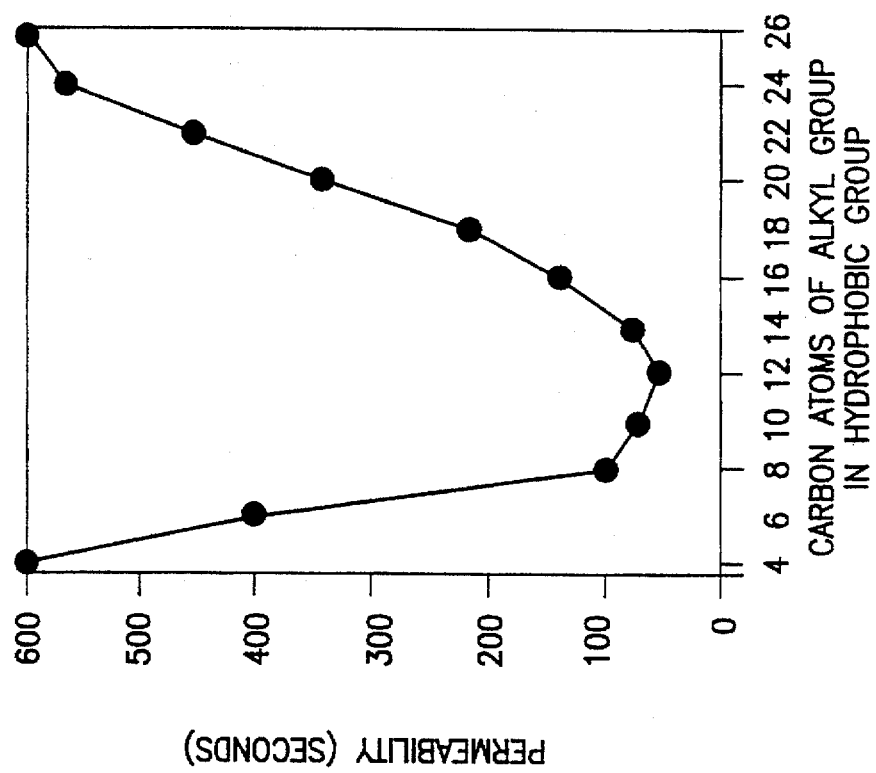
FIG. 3 is a graph showing the relationship of the number of carbon atoms in the hydrophobic group of the surface-active agent contained in the detergent composition vs. permeability (in seconds).

As is apparent from the test results as shown in FIG. 3, the composition of the surface-active agent having the alkyl group having from 6 to 24 carbon atoms in the hydrophobic group gave a good degree of permeability.

Example 7

A mixture was prepared containing a sodium salt of polyethylene glycol-alpha-sulfo-myristic acid mono-ester (A) and a di-sodium salt of polyethylene glycol-alpha-sulfo-myristic acid di-ester (B) in the ratio of the ester (A) to the ester (B) of 25 to 75, and there was formulated a composition of the surface-active agent having a variety of chain lengths of the hydrophobic group. The surface-active agent composition was then measured for its permeability in the same manner as in Example 4, thereby determining the influence of the degree of polymerization of the polyol upon the permeability of the composition. The test results are shown in FIG. 4.

Figure 4:
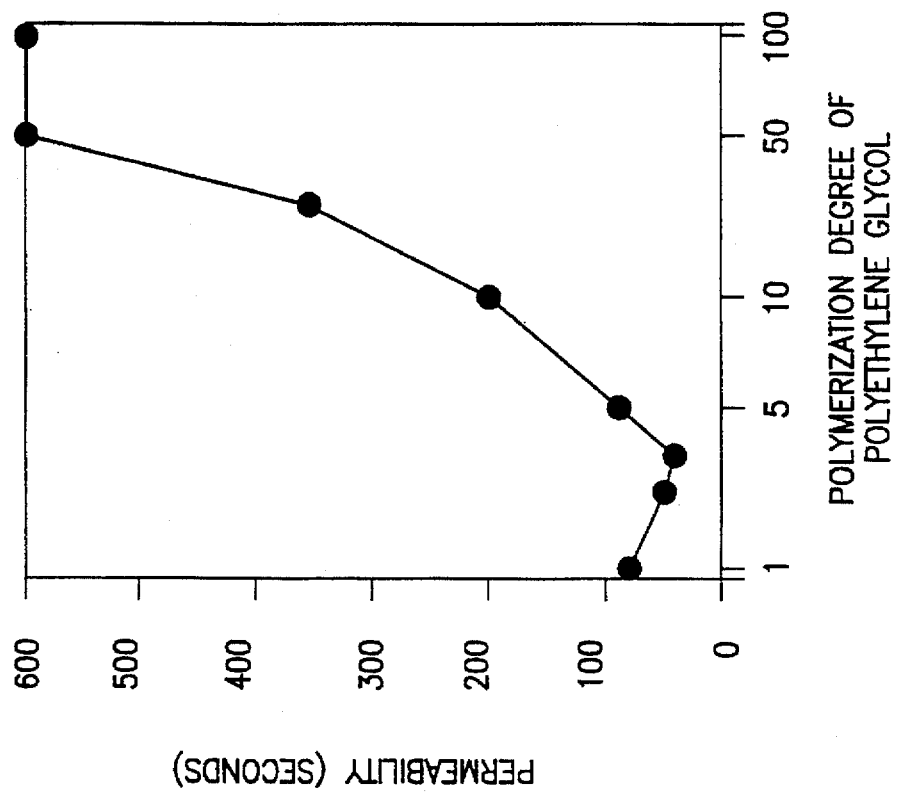
FIG. 4 is a graph showing the relationship of the degree of polymerization of polyethylene glycol in the surface-active agent contained in the detergent composition vs. permeability (in seconds).

As is apparent from the test results as shown in FIG. 4, the composition of the surface-active agent having the degree of polymerization ranging from 1 to 50 in the polyethylene glycol gave a good degree of permeability.

Example 8

Detergent for washing tableware

A detergent (pH 6.5) for washing tableware was prepared having the composition as follows:

| Ingredients | Percentage (%) by weight |
|---|---|
| Sodium salt of polyoxyethylene glycol (9)-alpha-sulfo-palmitic acid mono-ester | 12.0 |
| Sodium salt of polyoxyethylene glycol (9)-alpha-sulfo-palmitic acid di-ester | 6.0 |
| Palm fatty acid di-ethanol amide | 3.0 |
| Polyoxyethylene glycol 400 | 3.0 |
| Ethanol | 2.0 |
| Yellow #203 | Very small |
| Flavor | Very small |
| Ion-exchanged water | Balance |

This detergent was found superior in resistance to hard water and it did not give any feel that the skin of the hands become rough or sore.

Example 9

Shampoo for washing the body

A detergent (pH 6.5) for washing the body was prepared having the composition as follows:

| Ingredients | Percentage (%) by weight |
|---|---|
| Sodium salt of polyoxyethylene glycol (4.5)-alpha-sulfo-myristic acid mono-ester | 15.0 |
| Sodium salt of polyoxyethylene glycol (4.5)-alpha-sulfo-myristic acid di-ester | 7.0 |
| Potassium myristate | 10.0 |
| Polyoxyethylene glycol 200 | 5.0 |
| β-Carotene | Very small |
| Flavor | Very small |
| Ion-exchanged water | Balance |

This shampoo gave a good and soft touch on the skin of the body after application.

Example 10

Shampoo for washing the body

A detergent (pH 6.5) for washing the body was prepared having the composition as follows:

| Ingredients | Percentage (%) by weight |
| --- | --- |
| Sodium salt of polyoxyethylene glycol (4)-monomethyl ether-alpha-sulfomyristic acid ester | 25.0 |
| Potassium myristate | 10.0 |
| Polyoxyethylene glycol 1000 | 5.0 |
| β-Carotene | Very small |
| Flavor | Very small |
| Ion-exchanged water | Balance |

This shampoo gave a good and soft touch on the skin of the body after application.

Example 11

Shampoo for washing the hair

A detergent (pH 6.0) for washing the hair was prepared having the composition as follows:

| Ingredients | Percentage (%) by weight |
| --- | --- |
| Sodium salt of polyoxyethylene glycol (3)-alpha-sulfomyristic acid mono-ester | 18.0 |
| Sodium salt of polyoxyethylene glycol (3)-alpha-sulfomyristic acid di-ester | 12.0 |
| Palm fatty acid di-ethanol amide | 3.0 |
| Palm fatty acid amido propyl-betaine | 4.0 |
| Triethylene glycol | 8.0 |
| Yellow #203 | Very small |
| Flavor | Very small |
| Ion-exchanged water | Balance |

This shampoo did not give a rough touch of the hair to the hands during washing the hair and it provided the hair with a good and soft feel after drying.

Example 12

Shampoo for washing the hair

A detergent (pH 6.0) for washing the hair was prepared having the composition as follows:

| Ingredients | Percentage (%) by weight |
| --- | --- |
| Sodium salt of polyoxyethylene glycol (3)-monomethyl ether-alpha-sulfopalmitic acid ester | 25.0 |
| Sodium salt of higher alcohol polyoxyethylene (5)-sulfuric acid ester | 5.0 |
| Propylene glycol | 5.0 |
| Yellow #203 | Very small |
| Flavor | Very small |
| Ion-exchanged water | Balance |

This shampoo did not give a rough touch of the hair to the hands during washing the hair and it provided the hair with a good and soft feel after drying.

Example 13

Detergent for washing kitchen appliances

A detergent (pH 6.5) for washing kitchen appliances was prepared having the composition as follows:

| Ingredients | Percentage (%) by weight |
| --- | --- |
| Sodium salt of polyoxyethylene glycol (9)-alpha-sulfopalmitic acid di-ester | 13.0 |
| Palm fatty acid di-ethanol amide | 3.0 |
| Ethanol | 1.0 |
| Yellow #203 | Very small |
| Flavor | Very small |
| Ion-exchanged water | Balance |

This detergent was found superior in resistance to hard water and it did not give a rough touch on the hands after application.

Example 14

Detergent for washing kitchen appliances

A detergent (pH 7.0) for washing kitchen appliances was prepared having the composition as follows:

| Ingredients | Percentage (%) by weight |
| --- | --- |
| Sodium salt of polyoxyethylene glycol (3)-mono-methyl ether-alpha-sulfo-myristic acid mono-ester | 15.0 |
| n-Dodecyl dimethyl amine oxide | 3.0 |
| Ethanol | 1.0 |
| Yellow #203 | Very small |
| Flavor | Very small |
| Ion-exchanged water | Balance |

This detergent was found superior in resistance to hard water and it did not give a rough touch on the hands after application.

Example 15

Shampoo for washing the body

A detergent (pH 6.5) for washing the body was prepared having the composition as follows:

| Ingredients | Percentage (%) by weight |
| --- | --- |
| Sodium salt of polyoxyethylene glycol (2)-alpha-sulfomyristic acid di-ester | 10.0 |
| Potassium myristate | 10.0 |
| β-Carotene | Very small |
| Flavor | Very small |
| Ion-exchanged water | Balance |

This shampoo provided the skin of the body with a good and soft touch after application.

Example 16

Shampoo for washing the hair

A shampoo (pH 6.0) for washing the hair was prepared having the composition as follows:

| Ingredients | Percentage (%) by weight |
| --- | --- |
| Sodium salt of polyoxy-ethylene glycol (3)-alpha-sulfo-palmitic acid di-ester | 12.0 |
| Palm fatty acid di-ethanol amide | 3.0 |
| Palm fatty acid amido propyl-betaine | 4.0 |
| Yellow #203 | Very small |
| Flavor | Very small |
| Ion-exchanged water | Balance |

This shampoo did not give a rough touch of the hair to the hands during washing the hair and it provided the hair with a good and soft feel after drying.

Example 17

Shampoo for washing the hair

A detergent (pH 6.0) for washing the hair was prepared having the composition as follows:

| Ingredients | Percentage (%) by weight |
| --- | --- |
| Sodium salt of polyoxy-ethylene glycol (4)-mono-methyl ether-alpha-sulfo-stearic acid mono-ester | 15.0 |
| Sodium salt of higher alcohol polyoxyethylene (5)-sulfuric acid ester | 5.0 |
| Propylene glycol | 5.0 |
| Yellow #203 | Very small |
| Flavor | Very small |
| Ion-exchanged water | Balance |

This shampoo did not give a rough touch of the hair to the hands during washing the hair and it provided the hair with a good and soft feel after drying.

Example 18

Detergent for washing household goods

A detergent (pH 7.0) for washing the housing goods was prepared having the composition as follows:

| Ingredients | Percentage (%) by weight |
| --- | --- |
| Sodium salt of polyoxy-ethylene glycol (9)-alpha-sulfo-myristic acid di-ester | 5.0 |
| Sodium salt of higher alcohol polyoxyethylene (7)-sulfuric acid ester | 1.0 |
| Yellow #203 | Very small |
| Flavor | Very small |
| Ion-exchanged water | Balance |

This detergent did not give any unpleasant feel to the skin when it touched on the body during or after application when household furniture or leather goods were washed with this detergent. Further, the detergent provided a high degree of washability.

Example 19

Detergent for washing a metal surface

A detergent (pH 7.0) for washing the surface of a metal was prepared having the composition as follows:

| Ingredients | Percentage (%) by weight |
| --- | --- |
| Sodium salt of polyoxy-ethylene glycol (3)-alpha-sulfo-lauric acid di-ester | 8.0 |
| Sodium salt of higher alcohol polyoxyethylene (7)-sulfuric acid ester | 2.0 |
| Yellow #203 | Very small |
| Flavor | Very small |
| Ion-exchanged water | Balance |

This detergent did not give any unpleasant feel to the skin when it touched on the body during or after application when the metal surface of the body of an automobile vehicle or the like was washed with this detergent. Further, the detergent provided a high degree of washability.

Example 20

The powdery or granular detergent compositions according to the present invention were evaluated in the manner as will be described hereinafter.

1. Method for the evaluation of washability (i) Preparation of artificial dirt

Inorganic dirt was prepared by drying clay containing calorinite and vermiculite (crystalline mineral) as a major ingredient at 200° C. for 30 hours.

Carbon black (0.25 gram) was dispersed with a high-power emulsifying machine POLYTRON® (product of Kinematica in Switzerland) in a solution of 3.5 grams of gelatin in 950 cc of water at about 40° C. Separately, 14.9 grams of the inorganic dirt was emulsified with the emulsifying machine, followed by adding 31.35 grams of organic dirt (having the composition as will be indicated in Table 4 hereinafter) to the emulsified inorganic dirt and then emulsifying the mixture with the emulsifying machine to thereby produce a stable dirt bath. In the dirt bath was immersed a 10 cm×20 cm clean cloth (Cotton Cloth #60), and the resulting cloth was squeezed with a rubber two-roll machine to remove water and make the amount of the dirt on the cloth uniform. The cloth was then dried at 105x C for 30 minutes and the both sides of the cloth were rubbed five times each in the rightand left directions. The cloth was then cut into 5 cm×5 cm pieces which were used to measure the reflectance. The cloth pieces having the reflectance of 42%±2% were chosen as test specimens. The composition of the artificial dirt on the test specimen is as follows:

TABLE 4

| DIRT INGREDIENT | AMOUNT (% by weight) |
| --- | --- |
| Organic Dirt: | |
| Oleic acid | 28.3 |
| Triolein | 15.6 |
| Cholesterol oleate | 12.2 |
| Liquid paraffin | 2.5 |
| Squalene | 2.5 |
| Cholesterol | 1.6 |
| TOTAL | 62.7 |
| Gelatin | 7.0 |
| Organic Dirt | 29.8 |
| Carbon Black | 0.5 |

(ii) Method for Washing and Evaluation

The washing was carried out with a full automatic washing machine with two tanks (Model: CW-225, product of Mitsubishi Electric Co., Ltd.). A dress shirt with 10 sheets of the cloth specimens sewn thereon was used as a sample.

Into the washing machine was poured 30 liters of tap water at 10x C, followed by the addition of the detergent so as to amount to a predetermined concentration and a total weight of 1 kilogram of the sample. The washing was conducted for 10 minutes. The concentration of the detergent was set to 0.133% when the detergent was prepared in accordance with Preparation Process A as will be described hereinafter and 0.0833% when the detergent was prepared in accordance with Preparation Process B as will be described hereinafter.

The shirts were then centrifuged for 1 minute to remove the water therefrom and then rinsed for 3 minutes, followed by centrifuging them for 1 minute and then rinsing them for 3 minutes. After drying, the specimen clothes were measured for reflectance and the washability was calculated by the formula as follows:

$$\text{Washability Rate (\%)} = \frac{K/S \text{ of Dirt Cloth} - K/S \text{ of Washed Cloth}}{K/S \text{ of Dirt Cloth} - K/S \text{ of Clean Cloth}} \times 100$$

$$K/S = (1 - R/100)^2 / (2R/100)$$

where R is the reflectance (%), as measured with the reflectiometer (ELREPHO (trademark), Karl Zeiss, Germany).

The washability was evaluated as a mean value of 10 sheets of the test cloth specimens.

2. Solubility

A beaker was supplied with 1 liter of water kept at 10° C., and a cell for measuring conductance was immersed into the water. Into each of the beakers was added 1 gram of each of the powdery or granular surface-active agent compositions having the composition as will be indicated in Table 5 hereinafter, and the mixture was stirred at 250 rpm with a constant-speed stirrer. The time required for dissolving 90% by weight of the detergent particles was measured as a dissolution time (T), represented in seconds. The conductance was measured with a conductance meter (Model: HORIBA CONDUCTIVE METER DS-8F, Horiba Seisakusho K.K).

3. Preparation of Powdery or Granular Detergent Compositions

The powdery or granular detergent compositions having the composition as will be indicated in Table 5 hereinafter were prepared in accordance with Preparation Process A or B as will be described hereinafter. The washability and solubility of the powdery or granular detergent compositions were evaluated in the manner as have been described hereinabove. The results are shown in Table 5 hereinafter.

(i) Preparation Process A:

A slurry containing all the ingredients but an enzyme was spray-dried to thereby produce powdery particles having a bulk density of from 0.3 gram/cc to 0.4 gram/cc, followed by the addition of the powdery enzyme to the particles.

(ii) Preparation Process B:

A slurry containing all the ingredients but an enzyme and a half volume of zeolite was spray-dried to thereby produce powdery particles having a bulk density of 0.38 gram/cc. The powder particles were then charged into a high-speed mixer, mixed with finely divided zeolite having some water content, and granulated into granules. The resulting granules were filtered through a 1 mm screen to thereby remove crude particles. To the powdery product were added small amounts of the powdery enzyme and finely divided zeolite, thereby producing the composition having a bulk density of from 0.70 gram/cc to 0.95 gram/cc.

In Table 5 hereinafter, the surface-active agents indicated therein are as follows:

Surface-Active Agent A: Di-sodium salt of polyoxyethylene glycol (5)-alpha-sulfo-lauric acid di-ester Surface-Active Agent B: Di-sodium salt of polyoxyethylene glycol (9)-alpha-sulfo-myristic acid di-ester Surface-Active Agent C: Di-sodium salt of polyoxyethylene glycol (10)-alpha-sulfo-palm fatty acid ($C_{10}$–$C_{16}$) di-ester.

Surface-Active Agent D: Di-sodium salt of polyoxyethylene glycol (10)-alpha-sulfo-palm fatty acid ($C_{10}$–$C_{16}$) di-ester Surface-Active Agent E: Sodium salt of polyoxyethylene glycol (9)-alpha-sulfo-lauric acid mono-ester Surface-Active Agent F: Sodium salt of polyoxyethylene glycol (9)-alpha-sulfo-myristic acid mono-ester Surface-Active Agent G: Sodium salt of polyoxyethylene glycol (10)-alpha-sulfo-palm fatty acid ($C_{10}$–$C_{16}$) mono-ester Surface-Active Agent I: Sodium salt of polyoxyethylene glycol (4) mono-ethyl ether-alpha-sulfo-palm fatty acid ($C_{10}$–$C_{16}$) ester AOS-Na: Sodium salt of alpha-olefin ($C_{14}$–$C_{18}$) sulfonic acid ester alpha-SFMe-Na: Sodium salt of alpha-sulfo-fatty acid ($C_{12}$–$C_{18}$) methyl ester LAS-Na: Sodium salt of a straight-chain alkyl ($C_{10}$–$C_{14}$)-benzene sulfonic acid NONION-1: EO-adduct type nonionic surface-active agent with ethylene oxide (EO) added to primary ($C_{12}$–$C_{13}$) alcohol at the average rate of 20 moles NONION-2: Nonionic surface-active agent of a fatty acid methyl ester with ethylene oxide (EO) added to methyl laurate at the mean rate of 15 moles Fluorescent Agent: A mixture of di-sodium 4,4-bis-(2-sulfo-styryl)-biphenyl and di-sodium 4-bis-[(4-toluidino-6-morpholino-1,3,5-triazin-2-yl)amino]stilbene-2,2-disulfonate (having the mixture ratio of 1:1)

Enzyme: A mixture of SABINASE® 6.0T/LIPOLASE® 100T (5:1) (products of NOVO)

The sample Nos. 1 to 8 are directed to the detergent compositions according to the present invention and the sample Nos. 9 and 10 are directed to the compositions for comparative purposes.

For the compounds as described herein, the number indicated between the parentheses behind the moiety "polyoxyethylene glycol" or the corresponding moiety is intended to mean an average mole number of the added ethylene oxide.

TABLE 5

| | | SAMPLE NOS. (% by weight) | | | | | | | | | |
|---|---|---|---|---|---|---|---|---|---|---|---|
| | | 1 | 2 | 3 | 4 | 5 | 6 | 7 | 8 | 9 | 10 |
| | | | | | | PREPARATION PROCESS | | | | | |
| | | A | A | B | B | B | B | B | B | A | B |
| (a) | Sodium salt of α-sulfo-fatty acid di-ester | | | | | | | | | | |
| | Surface-active agent A | 10 | — | 16 | — | — | — | — | — | — | — |
| | Surface-active agent B | — | — | — | 9 | — | — | — | — | — | — |
| | Surface-active agent C | — | 6 | — | — | 9 | — | — | — | — | — |
| | Surface-active agent D | — | — | — | — | — | 10 | 10 | 1 | — | — |
| (b) | Sodium salt of α-sulfo-fatty acid mono-ester | | | | | | | | | | |
| | Surface-active agent E | 1 | — | 2 | — | — | — | — | — | — | — |
| | Surface-active agent F | — | — | — | 9 | — | — | — | — | — | — |
| | surface-active agent G | — | 6 | — | — | 9 | — | — | — | — | — |
| | Surface-active agent H | — | — | — | — | — | 5 | — | — | — | — |
| | Surface-active agent I | — | — | — | — | — | — | 5 | 17 | — | — |
| (c) | Other Surface-Active Agents | | | | | | | | | | |
| | AOS—Na | 1 | — | — | — | — | 3 | 3 | — | 1 | 15 |
| | α-SFMe—Na | — | — | — | — | — | — | — | — | 11 | 4 |
| | LAS—Na | — | 2 | — | — | — | — | — | — | — | 1 |
| | NONION-1 | — | — | 3 | — | 3 | — | — | 3 | — | 1 |
| | NONION-2 | — | — | — | 3 | — | 3 | 3 | — | — | — |
| (d) | Accessory Ingredients | | | | | | | | | | |
| | A-type zeolite | 13 | 13 | 20 | 20 | 20 | 20 | 20 | 20 | 13 | 20 |
| | Sodium carbonate | 16 | 16 | 25 | 25 | 25 | 25 | 25 | 25 | 16 | 25 |
| | Potassium carbonate | — | — | 5 | 5 | 5 | 5 | 5 | 5 | — | 5 |
| | Sodium silicate | 3 | 3 | 5 | 5 | 5 | 5 | 5 | 5 | 3 | 5 |
| | Sodium sulfite | 1 | 1 | 2 | 2 | 2 | 2 | 2 | 2 | 1 | 2 |
| | Fluorescent agent | 0.3 | 0.3 | 0.5 | 0.5 | 0.5 | 0.5 | 0.5 | 0.5 | 0.3 | 0.5 |
| | Enzyme | 1.0 | 1.0 | 2.0 | 2.0 | 2.0 | 2.0 | 2.0 | 2.0 | 1.0 | 2.0 |
| | Glauber's salt | | | | | BALANCE | | | | | |
| | Water | | | | | 4–8 | | | | | |
| | Bulk Density (gram/cc) | 0.4 | 0.3 | 0.8 | 0.8 | 0.9 | 0.8 | 0.9 | 0.8 | 0.3 | 0.9 |
| | Evaluation Results | | | | | | | | | | |
| | Dissolution Time T (seconds) | 30 | 20 | 45 | 40 | 40 | 45 | 45 | 50 | 70 | 100 |
| | Washability (%) | 81 | 80 | 81 | 83 | 81 | 83 | 82 | 80 | 79 | 72 |

Example 21

Powder detergent for washing clothes

The powder detergent for washing clothes was prepared having the composition as follows:

| Ingredients | Percentage (%) by weight |
|---|---|
| Sodium salt of mono-ethylene glycol-alpha-sulfo-palmitic acid acid di-ester | 20.0 |
| Sodium alpha-C$_{14}$olefin sulfonate | 5.0 |
| Flake Marseille soap | 5.0 |
| Alcohol ethoxylate | 5.0 |
| Zeolite | 20.0 |
| Potassium carbonate | 15.0 |
| Sodium carbonate | 23.5 |
| Enzyme | 0.5 |
| Water content | 6.0 |

The detergent provided a sufficiently high degree of washability at the rate of 200 ppm with respect to the tank volume, corresponding to 60% of the standard concentration of a detergent to be used in usual cases.

Example 22

Detergent for washing kitchen appliances

The detergent (pH 7.0) for washing kitchen appliances was prepared having the composition as follows:

| Ingredients | Percentage (%) by weight |
|---|---|
| Sodium salt of mono-ethylene glycol-alpha-sulfo-lauric acid di-ester | 16.0 |
| Lauric acid di-ethanol amide | 3.0 |
| n-Dodecyl dimethyl amine oxide | 1.0 |
| Ethanol | 1.0 |
| Yellow #203 | Very small |
| Flavor | Very small |
| Ion-exchanged water | Balance |

This detergent was found superior in resistance to hard water and it did not give any feel that the skin of the hands become rough or sore. Effective washability was also achieved at low concentrations.

Example 23

Shampoo for washing the body

A shampoo (6.5) for washing the body was prepared having the composition as follows:

| Ingredients | Percentage (%) by weight |
| --- | --- |
| Potassium salt of mono-ethylene glycol-alpha-sulfo-myristic acid di-ester | 20.0 |
| Potassium myristate | 5.0 |
| Polyethylene glycol 200 | 5.0 |
| β-Carotene | Very small |
| Flavor | Very small |
| Ion-exchanged water | Balance |

This shampoo gave a good and soft touch on the skin of the body after application. Washable performance was achieved even at the low concentrations.

Example 24

Shampoo for washing the hair

A shampoo (pH 6.0) for washing the hair was prepared having the composition as follows:

| Ingredients | Percentage (%) by weight |
| --- | --- |
| Sodium salt of mono-ethylene glycol-alpha-sulfo-palmitic acid di-ester | 14.0 |
| Palm fatty acid di-ethanol amine | 5.0 |
| Palm fatty acid amido propyl-betaine | 4.0 |
| Yellow #203 | Very small |
| Flavor | Very small |
| Ion-exchanged water | Balance |

This shampoo did not give a rough touch of the hair to the hands during washing the hair and it provided the hair with a good and soft feel after drying. Washable performance was achieved even at the low concentrations.

Example 25

Detergent for washing household goods

A detergent (pH 7.0) for washing the housing materials and household ware was prepared having the composition as follows:

| Ingredients | Percentage (%) by weight |
| --- | --- |
| Sodium salt of mono-ethylene glycol-alpha-sulfo-myristic acid di-ester | 5.0 |
| Sodium salt of higher alcohol polyoxyethylene (5)-sulfuric acid ester | 1.0 |
| Amidopropyl-betaine | 1.0 |
| Yellow #203 | Very small |
| Flavor | Very small |
| Ion-exchanged water | Balance |

This detergent did not give any unpleasant feel to the skin when it touched on the body during or after application when household furniture or leather goods were washed or rinsed with this detergent. Further, the detergent provided a high degree of washability. In addition, good washable performance was achieved even at low concentrations.

Example 26

Detergent for washing a hard surface

A detergent (pH 7.0) for washing the surface of a hard material was prepared having the composition as follows:

| Ingredients | Percentage (%) by weight |
| --- | --- |
| Sodium salt of polyoxy-ethylene glycol-alpha-sulfo-stearic acid di-ester | 7.5 |
| Sodium salt of higher alcohol polyoxyethylene (3)-sulfuric acid ester | 2.5 |
| Yellow #203 | Very small |
| Flavor | Very small |
| Ion-exchanged water | Balance |

This detergent did not give any unpleasant feel to the skin when it touched on the body during or after application when the hard surface of a hard material such as the body of an automobile vehicle was washed or rinsed with this detergent. Further, the detergent provided a high degree of washability.

Example 27

Powder detergent for washing clothes

The powder detergent for washing clothes was prepared having the composition as follows:

| Ingredients | Percentage (%) by weight |
| --- | --- |
| Sodium salt of propylene glycol-alpha-sulfo-myristic acid di-ester | 22.5 |
| Potassium alkyl-benzene sulfonate | 10.0 |
| Alcohol ethoxylate | 5.0 |
| Zeolite | 22.0 |
| Potassium carbonate | 5.0 |
| Sodium silicate | 10.0 |
| Sodium carbonate | 23.5 |
| Enzyme | 5.0 |
| Water content | 5.0 |

The powder detergent is found superior in the ability of preventing re-staining the clothes and it provides highly washable performance.

Example 28

Detergent for washing housing goods, etc.

The detergent (pH 7.0) was prepared having the composition as follows:

| Ingredients | Percentage (%) by weight |
| --- | --- |
| Sodium salt of isopropylene glycol-alpha-sulfo-stearic acid di-ester | 5.0 |
| Polyoxyethylene (5) dodecyl ether | 2.5 |
| Yellow #203 | Very small |
| Flavor | Very small |
| Ion-exchanged water | Balance |

This detergent was found high in the ability of preventing re-staining the housing goods and household ware. It demonstrated a high degree of washable performance and the skin of the hands did not become rough or sore even if it was brought into touch with the hands.

Example 29

Powder detergent for washing clothes

The powder detergent for washing clothes was prepared having the composition as follows:

| Ingredients | Percentage (%) by weight |
|---|---|
| Sodium salt of propylene glycol-alpha-sulfo-myristic acid di-ester | 22.5 |
| Potassium alkyl-benzene sulfonate | 10.0 |
| Alcohol ethoxylate | 5.0 |
| Zeolite | 22.5 |
| Potassium carbonate | 5.0 |
| Sodium silicate | 10.0 |
| Sodium carbonate | 23.5 |
| Enzyme | 0.5 |
| Water content | 6.0 |

The powder detergent is found superior in the ability of preventing re-staining the clothes and it provides good washable performance.

Example 30

Detergent for washing housing goods, etc.

The shampoo (pH 7.0) for washing housing goods and household ware was prepared having the composition as follows:

| Ingredients | Percentage (%) by weight |
|---|---|
| Sodium salt of isopropylene glycol-alpha-sulfo-stearic acid di-ester | 5.0 |
| Polyoxyethylene (5) dodecyl ether | 2.5 |
| Yellow #203 | Very small |
| Flavor | Very small |
| Ion-exchanged water | Balance |

This detergent was found high in the ability of preventing re-staining the housing goods and household ware. It demonstrated a high degree of washable performance and the skin of the hands did not become rough or sore even if it was brought into touch with the hands.

Example 31

Powder detergent for washing clothes

The powder detergent for washing clothes was prepared having the composition as follows:

| Ingredients | Percentage (%) by weight |
|---|---|
| Sodium salt of mono-ethylene-glycol-alpha-sulfo-myristic acid di-ester | 20.0 |
| Sodium salt of mono-ethylene-glycol-alpha-sulfo-myristic acid mono-ester | 10.0 |
| Mono-ethylene glycol | 5.0 |
| Zeolite | 21.5 |
| Potassium carbonate | 5.0 |
| Sodium silicate | 12.0 |
| Sodium carbonate | 20.5 |
| Enzyme | 0.5 |
| Water content | 6.0 |

The powder detergent is found superior in permeability and wettability. Further, it achieved good washable performance.

Example 32

Detergent for treating fibers

The detergent for treating fibers was prepared having the composition as follows:

| Ingredients | Percentage (%) by weight |
|---|---|
| Sodium salt of polyethylene (10)-polypropylene (3)-glycol-alpha-sulfo-palmitic acid di-ester | 2.5 |
| Sodium salt of polyethylene (10)-polypropylene (3)-glycol-alpha-sulfo-palmitic acid mono-ester | 0.5 |
| Polyethylene (10)-polypropylene (3)-glycol | 1.0 |
| Ion-exchanged water | Balance |

This detergent was found superior in permeability and wettability for fibers and provided a high degree of wettable effects. Further, this detergent was very low in bubbling.

Examples 33–39

A four-necked flask was charged with 2.0 moles of a lower alkyl-alpha-sulfo-fatty acid ester and 2.0 moles of a polyvalent alcohol, and the mixture was mixed to give a solution which in turn was subjected to ester interchange reaction at 100x C at reduced pressure (100 torr (133.32 hPa)) for 1.5 hours. The reaction results are shown in Table 6 herein-after.

Comparative Example 1

A four-necked flask was charged with 2.0 moles of an alpha-sulfo-lauric acid, 2.0 moles of polyethylene glycol and 1.5 liters of toluene (as a reaction solvent) and the mixture was mixed to give a solution which in turn was subjected to dehydration condensation esterification at 100x C at reduced pressure (100 torr) for 1.5 hours. The reaction results are shown in Table 6 hereinafter..

The tone of color and the reactivity of the reaction product were analyzed in the manner as will be described hereinafter.

1. Tone of color:

A 10% aqueous solution of the reaction mixture was prepared and the absorbance of the sample solution was measured at 420 nm with a spectrophotometer. The tone of color of the sample solution was calculated by the formula as follows:

$$color\ tone = Absorbance\ (-\log T) \times 1{,}000$$

2. Reactivity

The reactivity was measured with high-speed liquid chromatography.

TABLE 6

| | LOWER ALKYL-α-SULFO-FATTY ACID ESTER | POLYVALENT ALCOHOL | REACTIVITY (%) | TONE OF COLOR |
|---|---|---|---|---|
| EXAMPLE 33 | Methyl-α-sulfo-lauric acid ester | Ethylene glycol | 95 | 72 |
| EXAMPLE 34 | Methyl-α-sulfo-lauric acid ester | Polyethylene glycol #400 | 94 | 70 |
| EXAMPLE 35 | Methyl-α-sulfo-myristic acid ester | Tripropylene glycol | 92 | 75 |
| EXAMPLE 36 | Methyl-α-sulfo-palmitic acid ester | Polypropylene glycol P-400 (Asahi Denka Kogyo) | 93 | 78 |
| EXAMPLE 37 | Methyl-α-sulfo-stearic acid ester | Ethylene glycol-propylene glycol block copolymer (Asahi Denka Kogyo) | 92 | 80 |
| EXAMPLE 38 | n-Propyl-α-sulfo-lauric acid ester | Polyethylene glycol #400 | 93 | 73 |
| EXAMPLE 39 | Methyl-α-sulfo-lauric acid ester | Polyethylene glycol #400 | 95 | 38 |
| COMPARATIVE EXAMPLE 1 | α-Sulfo-lauric acid | Polyethylene glycol #400 | 68 | 128* |

*) Measured after toluene has been distilled off under reduced pressure

Example 40

A four-necked flask was charged with 1.5 moles of methyl-alpha-sulfo-lauric acid ester and 1.5 moles of tripropylene glycol, and the mixture was mixed to give a solution which in turn was subjected to ester interchange reaction at 90° C. at ambient pressure for 1 hour. The reaction results are shown in Table 7 hereinafter.

Comparative Examples 2–3

A four-necked flask was charged with 1.5 moles of methyl-alpha-sulfo-lauric acid ester and 1.5 moles of tripropylene glycol, and the mixture was mixed to give a solution which in turn was subjected to ester interchange reaction at 70° C. and 160° C., respectively, at ambient pressure for 2 hours. The reaction results are shown in Table 7 hereinafter.

Examples 42–43

A four-necked flask was charged with ethyl-alpha-sulfo-palmitic acid ester and polypropylene glycol in the molal ratios of 1:2, 1:1, and 2:1, respectively, and the mixture was mixed to give a solution which in turn was subjected to ester interchange reaction at 120° C. at reduced pressure (150 torr (199.98 hPa)) for 2.5 hours. The reaction results are shown in Table 8 hereinafter.

The ratio of the polyethylene #300-alpha-sulfo-palmitic acid mono-ester to the polyethylene #300-alpha-sulfo-palmitic acid di-ester in the reaction mixture was measured with the aid of a high-speed liquid column chromatography.

TABLE 7

| | REACTION TEMPERATURE (°C.) | REACTIVITY (%) | TONE OF COLOR |
|---|---|---|---|
| EXAMPLE 40 | 90 | 96 | 74 |
| COMPARATIVE EXAMPLE 2 | 70 | 37 | 30 |
| COMPARATIVE EXAMPLE 3 | 160 | 95 | 443 |

TABLE 8

| | MOLAR RATIO OF RAW MATERIALS | MOLAR RATIO OF MONO-ESTER TO DI-ESTER | TONE OF COLOR |
|---|---|---|---|
| EXAMPLE 41 | 1:2 | 87:13 | 70 |
| EXAMPLE 42 | 1:1 | 72:28 | 72 |
| EXAMPLE 43 | 2:1 | 32:68 | 75 |

The detergent compositions according to the present invention are low in irritability to the body and superior in washing and cleansing characteristics. Particularly, the detergent compositions containing the alpha-sulfo-fatty acid derivatives as represented by the general formula (2) are very low in irritability to the body and low in the critical micelle concentration.

The detergent compositions according to the present invention offers the advantages that, when the compositions are used in the form of liquid, periodical stability of the compositions is improved, and the ingredient of the compositions are unlikely to be separated, and no ingredients of the compositions are caused to be crystallized, because the alpha-sulfo-fatty acid derivatives as represented by the general formula (2), or (3) to be contained in the compositions have each a low Krafft point.

Further, the detergent compositions according to the present invention offers the advantages that, when the compositions are used in the form of powder or granules, their solubility in water can be so highly improved that they are particularly suitable for use in washing and rinsing clothes, because the alpha-sulfo-fatty acid derivatives as represented by the general formula (1), (2) or (3) to be contained in the compositions are each remarkably soluble in water.

In addition, the detergent compositions according to the present invention are so low in irritability to the body that they can be suitably employed for detergents to be used in a state that they are in contact with the skin of the body. Hence, the detergent compositions according to the present invention can advantageously be employed as liquid detergents for washing the body or part of the body, such as shampoos for washing the body and the hair and for washing the surface of a hard material, wooden material or leather goods. The surface of the hard material may include, for example, the surface of dishes, a metal surface, a plastic surface and a ceramic surface. The surface of the wooden material may include, for example, household furniture and pillars. As the leather goods, there may be mentioned, for example, handbags and boots.

The detergent compositions according to the present invention may be used in the form of solid, powder, paste or liquid.

We claim:

1. A detergent composition comprising, as an essential ingredient, at least one member selected from alpha-sulfo-fatty acid derivatives represented by the following formulas (1) and (2):

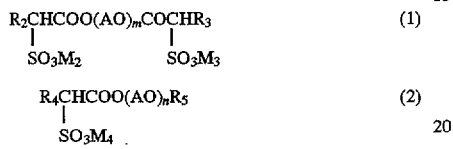

wherein $R_2$ and $R_3$ are each an alkyl group or an alkenyl group, each having from 6 to 24 carbon atoms;

$R_4$ is an alkyl group having from 6 to 24 carbon atoms;

$R_5$ is an alkyl group having from 1 to 4 carbon atoms;

$M_2$, $M_3$ and $M_4$ are each hydrogen atom or a cation capable of forming a salt;

AO is an oxyalkylene group; and m and n are each a positive integer.

2. A detergent composition as claimed in claim 1, wherein said essential ingredient is an alpha-sulfo-fatty acid derivative represented by the formula (2).

3. A detergent composition as claimed in claim 2 wherein said essential ingredient is present in an amount of 1 to 50% by weight.

4. A detergent composition as claimed in claim 1 wherein said essential ingredient is present in an amount of 1 to 50% by weight.

5. A detergent composition as claimed in claim 2, further comprising an auxiliary ingredient which is a mono-ester represented by the following formula (3):

wherein $R_1$ is an alkyl group or an alkenyl group each having from 6 to 24 carbon atoms;

$M_1$ is a hydrogen atom or a cation capable of forming a salt;

AO is an oxyalkylene group; and p is a positive integer.

6. A detergent composition as claimed in claim 5, wherein the weight ratio of said essential ingredient to said auxiliary ingredient is from 5:95 to 95:5.

7. A detergent composition as claimed in claim 5, further comprising a polyvalent alcohol.

8. A detergent composition as claimed in claim 6, further comprising a polyvalent alcohol.

9. A detergent composition as claimed in claim 1 wherein said cation capable of forming a salt is an alkali metal ion, an alkaline earth metal ion, an ammonium ion or a substituted ammonium ion.

10. A detergent composition as claimed in claim 1 wherein said composition is in the form of a liquid.

11. A detergent composition as claimed in claim 1 wherein said composition is in the form of a solid.

12. A process for the preparation of a mixture of alpha-sulfo-fatty acid derivatives represented by the following formulas (1) and (2):

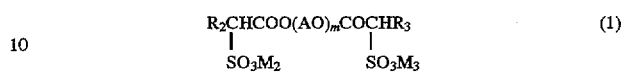

wherein $R_2$ and $R_3$ are each an alkyl group or an alkenyl group, each having from 6 to 24 carbon atoms;

$R_4$ is an alkyl group having from 6 to 24 carbon atoms;

$R_5$ is an alkyl group having from 1 to 4 carbon atoms;

$M_2$, $M_3$ and $M_4$ are each a hydrogen atom or a cation capable of forming a salt;

AO is an oxyalkylene group; and m and n are each a positive integer;

comprising reacting an alpha-sulfo-fatty acid alkyl ester represented by the following general formula (4):

wherein $R_6$ is an alkyl group or an alkenyl group, each having from 6 to 24 carbon atoms; and $R_7$ is an alkyl group having from 1 to 3 carbon atoms, with a glycol selected from alkylene glycols and polyalkylene glycols at a temperature of from 80° C. to 150° C.

13. A process as claimed in claim 12, wherein said reaction is performed in the absence of a solvent.

14. A process as claimed in claim 12, wherein said reaction is performed in the presence of an organic solvent having a boiling point of 200° C. or lower.

15. A process as claimed in claim 14, wherein said solvent is a lower alcohol.

16. A process as claimed in claim 12, wherein said alpha-sulfo-fatty acid alkyl ester is bleached prior to said reaction.

17. A process as claimed in claim 13, wherein said alpha-sulfo-fatty acid alkyl ester is bleached prior to said reaction.

18. A process as claimed in claim 14, wherein said alpha-sulfo-fatty acid alkyl ester is bleached prior to said reaction.

19. A process as claimed in claim 15, wherein said alpha-sulfo-fatty acid alkyl ester is bleached prior to said reaction.

20. A process as claimed in claim 13, wherein the molar ratio of said alpha-sulfo-fatty acid alkyl ester to said glycol is 1:3 to 3:1 and wherein said reaction is carried out under a reduced pressure while removing, by distillation, a lower alcohol $R_7OH$ (where $R_7$ is as defined above) formed in situ.

* * * * *

UNITED STATES PATENT AND TRADEMARK OFFICE
CERTIFICATE OF CORRECTION

PATENT NO. : 5,681,803
DATED : October 28, 1997
INVENTOR(S) : OKANO et al

It is certified that error appears in the above-indentified patent and that said Letters Patent is hereby corrected as shown below:

On the Title page, item [56]:

ON PAGE 2 OF THE PATENT: Under the heading "U.S. PATENT DOCUMENTS", "U.S. 4,472,282" should read --U.S. 4,472,287-- and "U.S. 4,707,289" should read --U.S. 4,707,789--.

Col. 14, line 53, "tauric" should read --lauric--.

Signed and Sealed this

Twenty-fourth Day of November, 1998

Attest:

BRUCE LEHMAN

Attesting Officer

Commissioner of Patents and Trademarks